United States Patent [19]

Cecere et al.

[11] Patent Number: 4,894,384
[45] Date of Patent: Jan. 16, 1990

[54] ALPHA-(1-TRIAZOLYL)-KETO-DERIVATIVES HAVING FUNGICIDAL ACTIVITY

[75] Inventors: Mirella Cecere; Franco Gozzo; Antonio Malandra; Luigi Mirenna, all of Milan, Italy

[73] Assignee: Montedison S.p.A., Milan, Italy

[21] Appl. No.: 165,382

[22] Filed: Feb. 29, 1988

Related U.S. Application Data

[63] Continuation-in-part of Ser. No. 913,314, Sep. 30, 1986, abandoned, which is a continuation of Ser. No. 556,336, Nov. 30, 1983, abandoned, which is a continuation-in-part of Ser. No. 500,360, Jun. 2, 1983, abandoned.

[30] Foreign Application Priority Data

Jun. 3, 1982 [IT] Italy ............................ 21665 A/82
Dec. 30, 1982 [IT] Italy ............................ 25048 A/82

[51] Int. Cl.⁴ ............... A01N 43/653; C07D 249/08
[52] U.S. Cl. .................................. 514/383; 548/262
[58] Field of Search ..................... 514/383; 548/262

[56] References Cited

U.S. PATENT DOCUMENTS 4,130,409 12/1978 Shephard et al. .................. 548/262
4,427,673 1/1984 Kramer et al. ..................... 548/101
4,472,395 9/1984 Kramer et al. ..................... 548/262
4,549,900 10/1985 Kramer et al. ..................... 548/262

FOREIGN PATENT DOCUMENTS 008458 3/1980 European Pat. Off. ............ 548/262

Primary Examiner—Richard L. Raymond
Assistant Examiner—Patricia L. Morris
Attorney, Agent, or Firm—Stevens, Davis, Miller & Mosher

[57] ABSTRACT

There are disclosed α-(1-triazolyl)-keto-derivatives of the general formula:

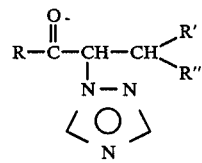

in which R is alkyl, alkenyl or phenyl optionally substituted; R" is alkoxycarbonyl, alkylcarbonyl, arylcarbonyl, aminocarbonyl or cyano; R' has the meanings of both R and R".

These compounds are endowed with high fungicidal activity.

4 Claims, No Drawings

ALPHA-(1-TRIAZOLYL)-KETO-DERIVATIVES HAVING FUNGICIDAL ACTIVITY

This application is a continuation-in-part of application Ser. No. 913,314, filed Sept. 30, 1986, which in turn is a continuation of application Ser. No. 556,336, filed Nov. 30, 1983, which in turn is a continuation-in-part of application Ser. No. 500,360, filed June 2, 1983, all now abandoned but the priorities of all of which are claimed.

BACKGROUND OF THE INVENTION

Triazolyl-derivatives endowed with fungicide activity are known in literature.

For instance, British patent application No. 1,511,956 (Imperial Chemical Industries) discloses triazolyl-diketoderivatives of the general formula:

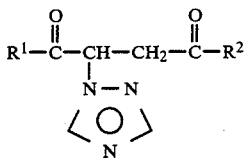

wherein $R^1$ and $R^2$, equal to each other or different from each other, may be a cycloalkyl, an alkyl or a phenyl group, any of which groups may be optionally substituted.

THE PRESENT INVENTION

We have now found α-(1-triazolyl)-keto-derivatives, which form an object of the present invention, having the general formula:

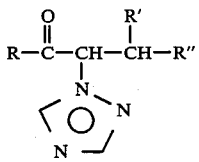

in which:

R represents a phenyl group optionally substituted by one or more groups selected from alkyl groups having from 1 to 4 carbon atoms, alkoxy groups having from 1 to 4 carbon atoms, halogen atoms, nitro and amino which last, in its turn, may be optionally substituted by 1 or 2 alkyl groups having from 1 to 4 carbon atoms, or R represents an alkyl group having from 1 to 6 carbon atoms, or an alkenyl group having from 2 to 6 carbon atoms optionally substituted by from 1 to 3 halogen atoms or by alkoxy groups having from 1 to 4 carbon atoms;

R″ represents an alkylcarbonyl group having from 1 to 4 carbon atoms in the alkyl; an alkoxycarbonyl group having from 1 to 4 carbon atoms in the alkoxy; an arylcarbonyl group, wherein the aryl is a phenyl optionally substituted by one or more groups selected from alkyl groups having from 1 to 4 carbon atoms, alkoxy groups having from 1 to 4 carbon atoms, halogen atoms, nitro and amino which last, in its turn, may be optionally substituted by 1 or 2 alkyl groups having from 1 to 4 carbon atoms; a cyano group; an aminocarbonyl group optionally substituted on the nitrogen atom by 1 or 2 groups selected from alkyl groups having from 1 to 4 carbon atoms and phenyl; R′, which may be equal to or different from R or R″, has the same meanings as both R and R″.

The compounds of formula I are endowed with a high fungicide activity and with other useful properties, hereinafter described, which allow to make use of such compounds in agriculture for protecting useful plants from the action of the phytopathogenous fungi.

A further object of the present invention consists in using the compounds of formula I as fungicides in agriculture and the fungicide compositions which contain said compounds as active ingredient.

Representative Examples of compounds falling under formula I are the compounds herebelow reported (the symbol "Tr" represents a 1,2,4-triazol-1-yl- radical).

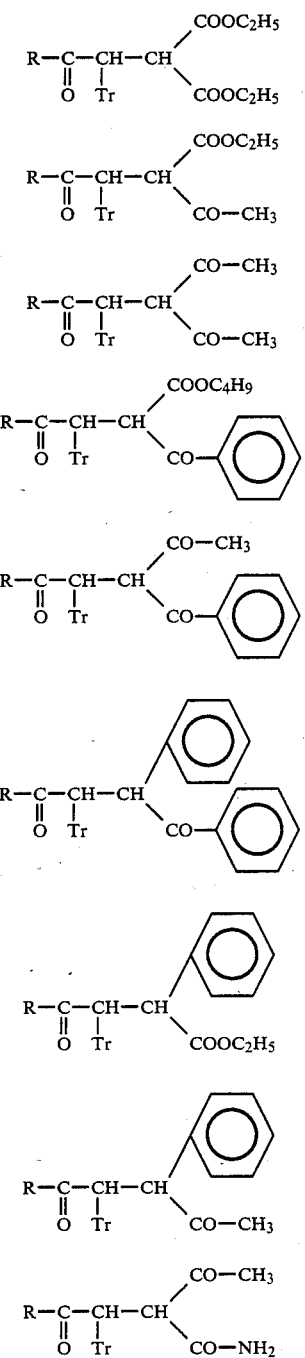

-continued

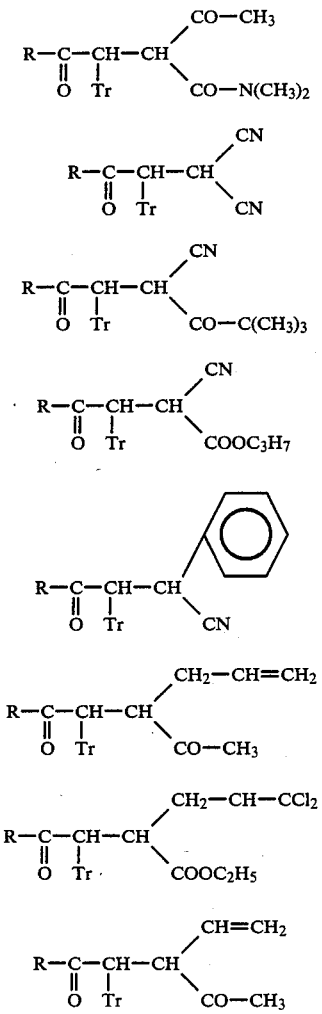

wherein R has the meanings given in formula I but preferably is an optionally substituted phenyl or an alkyl.

In the herebelow reported description of the processes for the preparation of the compounds of formula I, the symbols R, R' and R" have the same meanings indicated formula I.

A first synthesis process consists in adding 1,2,4-triazole to α-β-unsaturated ketones of formula II, according to reaction 1.

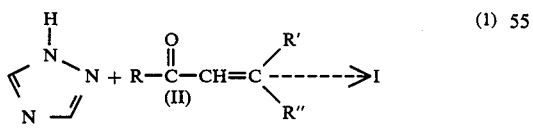

Reaction 1 is carried out in an inert solvent such as an aromatic hydrocarbon, for instance toluene, in the presence of a catalytic amount of an organic base, for instance a tertiary amine.

Alternatively, the reaction may be carried out in a polar solvent such as dimethylformamide in the presence of an inorganic base such as an alkaline carbonate or hydroxide, in particular potassium hydroxide.

Some of the compounds of formula II are known or they can be easily prepared according to methods which are available in the chemical literature (see, for instance for R=R'=C$_6$H$_5$ and R"=CO—C$_6$H$_5$; Beilstein 7 H 835 and the following ones).

However, the compounds of formula II in which R' is an alkylcarbonyl or alkoxycarbonyl group (e.g. the compounds reported in Table 1 herein after) are new and represent a further object of the invention.

A useful synthesis process for preparing the compounds of formula II wherein:

R' is an optionally substituted phenyl group or an optionally substituted alkyl or alkenyl group.

R is an optionally substituted phenyl group or a tertiary alkyl group, consists in reacting, according to a condensation reaction known in the literature (see for instance the already cited bibliographic reference) a suitable methyl-ketone with a ketone of the formula R'—CO—R", according to the following equation:

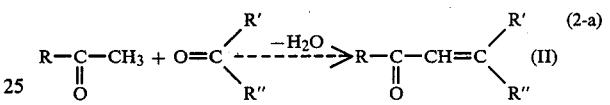

Reaction 2-a) is carried out by heating the mixture of the two ketones in the presence of a base, preferably potassium hydroxide in alcoholic solution.

A general process for preparing the compounds of formula II consists in reacting the suitable glyoxal

with a compound having an active methylene group, according to condensation reaction analogous to the preceding one:

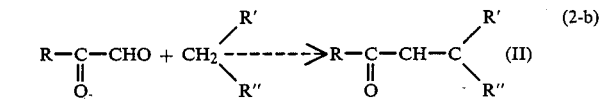

Glyoxals of formula R—CO—CHO are known compounds or they can be easy prepared, for instance, according to the procedure described by P. Karrer and C. Musante in Helvetica Chimica Acta 18, 1140 (1935).

An alternative synthesis for preparing the compounds of formula I consists in reacting an α-halo-ketone of the formula:

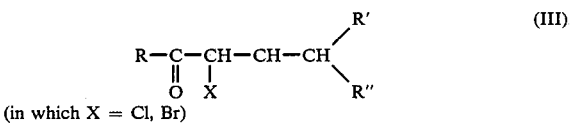

(in which X = Cl, Br)

with 1,2,4-triazole in the presence of a base, according to equation 3.

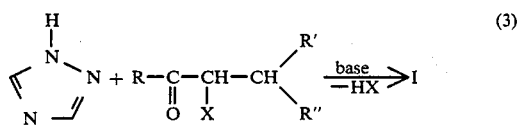

Reaction 3 is carried out in an inert solvent (for instance tetrahydrofuran) in the presence of a stoichiometric amount of an inorganic or an organic base (for instance triethylamine) and at a temperature comprised between the room temperature, and the boiling temperature of the reaction mixture.

The α-halo-ketones of formula III can be prepared by halogenation of the compounds of formula IV, according, to reaction 4:

$$R-\underset{O}{\underset{\|}{C}}-CH_2-CH\overset{R'}{\underset{R''}{\diagdown}} \xrightarrow[-HBr]{Br_2} III \quad (4)$$

(IV)

[see for instance Chi-Kang Dien et al, J. Org. Chem. 21 1492 (1956)].

The compounds of formula IV, in their turn, are prepared according to methods, which are known in literature, for instance by reacting an α-halo-ketone of formula V with a compound having an active methylenic group of formula VI according to reaction 5.

$$R-\underset{O}{\underset{\|}{C}}-CH_2X + R'-CH_2-\underset{O}{\underset{\|}{C}}-Y \xrightarrow{-HX} IV$$

(V)      (VI)

(in which X = Cl, Br and $-\underset{O}{\underset{\|}{C}}-Y = R''$).

Reaction 5 is carried out by reacting the compound of formula VI with sodium ethylate at the reflux temperature and by successively adding at room temperature the compound of formula V.

Both compounds of formula V and compounds of formula VI are known compounds or they can be easy prepared according to known techniques.

A third process for the synthesis of the compounds of formula I consists in reacting the suitable α-triazolyl-ketone in the form of sodium salt (VI) with a bromoderivative (VII) according to the following equation:

$$R-\underset{\underset{N\diagdown_N}{\overset{O}{\underset{\|}{C}}}{\underset{\|}{}}}{\underset{\|}{C}}-CH^{\ominus}Na^{\oplus}(VI) + Br-CH\overset{R'}{\underset{R''}{\diagdown}} (VII) \xrightarrow{-NaBr} I \quad (6)$$

It is evident to a person skilled in the art, that the compounds of formula I can exist in various isomeric forms, owing to the presence of assimetric centres.

The preparation carried out according to the above described methods, generally provides mixtures of isomers, which optionally may be separated according to conventional techniques.

Both isomeric mixtures and single isomers of the compounds of formula I fall within the scope of the present invention.

As herein before mentioned, the compounds of formula I are endowed with a high fungicide activity.

They possess a wide activity range, since they are active against phytopathogenous fungi belonging to various genera of numerous families such as for instance: Piricularia, Puccinia, Erysiphe, Sphaerotheca, Botrytis, Phytophtora, Venturia, Fusarium, Plasmopara, Peronospora, Pythium and others.

Therefore the compounds of formula I are useful for fighting numerous plant deseases, and they result to be particularly active against those deseases, which are generally known as oidium (or mildew) and rust (or blight).

Against these deseases the compounds according to the invention result to be endowed with a very high or complete activity, even at doses at which compounds according to British Pat. No. 1,511,936 result to be completely inactive.

Furthermore the compounds of formula I possess other positive characteristics such as a fungicide action, having both preventive and curative character and a complete compatibility with the plants to be protected against fungus infections.

Owing to the high fungicide activity coupled with the above mentioned positive characteristics, the compounds object of the present invention may be used for protecting a great number of useful cultivations from fungus infections. Among these useful cultivations we can cite: vine, rice, Gramineae, tomato, tobacco and other Solanaceae, horticultural cultivations, strawberries, Cucurbitaceae, fruit trees and ornamental plants. They can be used for protecting food-stuff as well.

For the practical uses in agriculture it is often useful to have available fungicide compositions containing one or more compounds of formula I as active ingredient.

Such compositions, which according to the normal formulative practice are in the form of dry powders, wettable powders, emulsifiable concentrates, pastes, granular formulates etc., consist of one or more compounds of formula I as active ingredient, of a solid or liquid carrier and optionally of other additives such as, for instance, surfactants, wetting agents, dispersing agents, suspending agents and the additives normally used in the formulative practice.

If desired, it is possible to add to the compositions object of the present invention other compatible active substances as well, such as other fungicides, herbicides, phytogrowth regulators, fertilizers and insecticides.

The dose of active substance to be used, varies as a function of different factors, such as the kind, the degree and the stadium of the fungus infection, the cultivation to be protected, the specific effectiveness of the considered compound of formula I, climatic and environmental factors.

Owing to the high fungicide activity of the compounds of formula I, it is generally sufficient to use amounts of active substance ranging from 10 to 2000 g/ha, preferably from 100 to 1500 g/ha.

The following examples are given to better illustrate the invention.

EXAMPLE 1

Preparation of ethyl α-benzoyl-β-(4-chlorobenzoyl)-acrylate

A solution containing 13.5 g of 4-chloro-phenylglyoxal and 15.4 g of ethyl benzoylacetate in 100 ml of anhydrous benzene was heated at the boiling temperature in the presence of a catalytic amount of piperidine (0.3 ml), till complete azeotropic distillation of the water formed during the reaction (about 6 hours).

The solution was cooled down to room temperature, washed with water and dried on sodium sulphate. After removal of the solvent at reduced pressures, an oily residue was obtained, which after having been diluted with a mixture of petroleum ether and diethyl ether in the ratio 1:1, yielded 18.9 g of a white solid (m.p. 122°–123° C.).

$^1$H NMR (CDCl$_3$, TMS): δ(ppm): 1.2 (3H, t, CH$_2$—CH$_3$); 4.2 (2H, q, CH$_2$—CH$_3$); 7.2–8.15 (10H, aromatic protons and —CH=). (t=triplet; q=quartet).

EXAMPLE 2

The compounds of formula II, reported in the following Table 1, were obtained by following a procedure analogous to that described in example 1, starting from the appropriate arylglyoxal and compound of formula: R′—CH$_2$—R″.

TABLE 1

Compounds of formula (I):

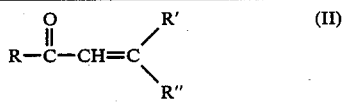

Notes to Table 1
1 Elemental analysis and $^1$H—NMR spectra of all the compounds are consistent with the assigned structure.
2 m.p. = Melting point (in degree centrigrade), b.p. = boiling point (in degrees centigrade) at the indicated pressure.
3 The preparation of compound 8 is described in detail in example 1.

EXAMPLE 3

Preparation of the ethyl ester of 2-benzoyl-3-[1-(1,2,4-triazolyl)]-3-(4-chlorobenzoyl)-propionic acid.

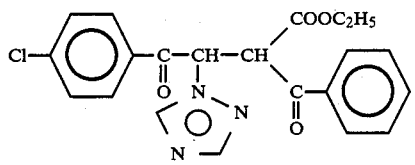

A solution containing 17.1 g of ethyl 2-benzoyl-3-(4-chlorobenzoyl)-acrylate [Compound No. 8 of Table 1] and 3.45 g of 1,2,4-triazole in 150 ml of toluene was reflux heated for 12 hours in the presence of a catalytic amount of triethylamine (0.5 ml).

The solution was cooled down to room temperature, washed with water and dried on sodium sulphate. After removal of the solvent at reduced pressure, a crude product was obtained, which after having been diluted with a small amount of cold ethyl ether, yielded 14.6 g of a white solid (m.p. 135°–136° C.).

$^1$H-NMR (CDCl$_3$, TMS) δ(ppm): 1.0 (3H, t, CH$_2$—CH$_3$) 3.95 (2H, q, CH$_2$—CH$_3$) 5.55 (1H, d, CH, J=11 Hz) 6.9 (1H, d, CH, J=11 Hz) 7.2–8.2 (10H, m, aromatic protons+CH triazole) 8.4 (1H, s, CH triazole). (s=singlet, d=doublet, t=triplet, q=quartet, m=multiplet or complex unresolved signal, J=coupling constant).

EXAMPLE 4

Preparation of 4-chlorophenyl-α-[1-(1,2,4-triazolyl)]-β-benzoyl-β-phenyl-ethyl-ketone [Compound No. 2]

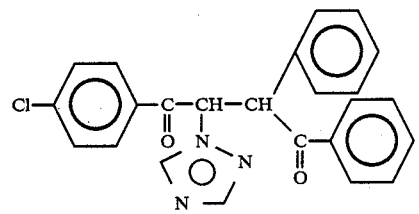

A mixture consisting of: 4.2 g of 1,2,4-triazole 14 g of 4-chlorophenyl-β-benzoyl-β-phenylvinyl-ketone

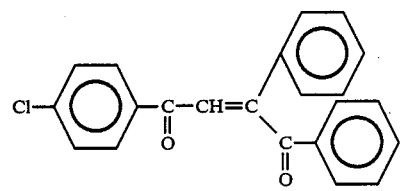

(prepared as described in Beilstein 7 E III 770)
0.5 ml of triethylamine
120 ml of toluene
was heated under reflux for 32 hours;

The mixture, after having been cooled down to room temperature, was washed with water and dried on anhydrous sodium sulphate. After elimination of the solvent by evaporation at reduced pressure, the crude product was subjected to chromatography on silica gel (eluent: n.hexane-ethylacetate in 8:1 ratio). 2.7 g of the desired product were so obtained (white solid, m.p. 195°–197° C. after crystallization from ethyl acetate and petroleum ether).

IR (nujol): significant bands at 1690 and 1655 cm$^{-1}$ (νC=O).

$^1$H-NMR (CDCl$_3$, TMS) δ(ppm): 5.70 (1H, d, CH, J=10 Hz) 6.65 (1H, d, CH, J=10 Hz) 7.10–8.25 (11H, m, aromatic and heterocyclic protons) (d=doublet, m=multiplet or unresolved complex signal, J=coupling constant).

EXAMPLE 5

The compounds of formula I, reported in the following Table 2, were prepared by operating according to the procedures described in examples 3 and 4, starting from the suitable intermediates and from 1,2,4-triazole.

TABLE 2

Compounds of formula (I):

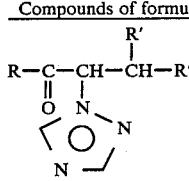

| Compound | R | R' | R'' | (2) m.p.(°C.) crystallization solvent | (3) IR (nujol) ($\nu$, cm$^{-1}$) |
|---|---|---|---|---|---|
| 2.1 | $C_6H_5$ | $COOC_2H_5$ | $COOC_2H_5$ | 131-2 (ethyl ether) | 1750, 1720, 1700 |
| 2.2 | $C_6H_5$ | $COOC_2H_5$ | $CO-C_6H_5$ | 91-3 (ethyl ether) | 1735, 1600, 1675 |
| 2.3 | $C_6H_5$ | $COOC_2H_5$ | $CO-CH_3$ | 114-5 (ethyl ether) | 1730, 1700, 1690 |
| 2.4 | $C_6H_5$ | $CO-CH_3$ | $CO-C_6H_5$ | 155-6 (petroleum ether) | 1715, 1680, 1670 |
| 2.5 | $4-Cl-C_6H_4$ | $COOC_2H_5$ | $COOC_2H_5$ | 123-4 (petroleum ether) | 1760, 1725, 1700 |
| 2.6[(4)] | $4-Cl-C_6H_4$ | $CO-C_6H_5$ | $COOC_2H_5$ | 135-5 (ethyl ether) | 1720, 1690, 1675 |
| 2.7 | $4-Cl-C_6H_4$ | $COOC_2H_5$ | $CO-CH_3$ | 106-8 (ethyl ether) | 1730, 1710, 1685 |
| 2.8 | $C_6H_5$ | $COOC_2H_5$ | $CO(4-Cl-C_6H_4)$ | 150-2 (ethyl alcohol) | 1720, 1695, 1675 |
| 2.9 | $4-Cl-C_6H_4$ | $COOC_2H_5$ | $CO(4-Cl-C_6H_4)$ | 92-4 (ethyl ether) | 1740, 1690, 1680 |
| 2.10 | $4-Cl-C_6H_4$ | $CO-CH_3$ | $CO-CH_3$ | 130-2 (petroleum ether) | 1725, 1690 |
| 2.11 | $C_6H_5$ | $C_6H_5$ | $CO-C_6H_5$ | 200-2 (petroleum ether) | 1690, 1655 |
| 2.12[(5)] | $4-Cl-C_6H_4$ | $C_6H_5$ | $CO-C_6H_5$ | 195-7 (ethylacetate-petroleum ether) | 1690, 1655 |
| 2.13 | $4-CH_3-C_6H_4$ | $C_6H_5$ | $CO-C_6H_5$ | 173-5 (petroleum ether) | 1680, 1660 |
| 2.14 | $4-CH_3O-C_6H_4$ | $C_6H_5$ | $CO-C_6H_5$ | 165-7 (ethyl ether) | 1685, 1660 |
| 2.15 | $4-F-C_6H_4$ | $COOC_2H_5$ | $CO-C_6H_5$ | semi-solid | 1735, 1685 |
| 2.16 | $2-Cl-C_6H_4$ | $COOC_2H_5$ | $CO-C_6H_5$ | 125-6 (ethylacetate-petroleum ether) | 1715, 1685, 1665 |
| 2.17 | $4-Cl-C_6H_4$ | $4-Cl-C_6H_4$ | $CO-(4-Cl-C_6H_4)$ | 212-4 (ethyl ether) | 1670, 1655 |
| 2.18 | $4-Cl-C_6H_4$ | $t.C_4H_9$ | $CO-C_6H_5$ | 146-8 (ethyl ether) | 1690, 1655 |
| 2.19 | $2-Cl-C_6H_4$ | $COOC_2H_5$ | $CO-(4-Cl-C_6H_4)$ | 125-6 (ethylacetate-petroleum ether) | 1715, 1685 |
| 2.20 | $C_6H_5$ | $t.C_4H_9$ | $CO-C_6H_5$ | 142-4 (ethyl ether) | 1675, 1655 |
| 2.21 | $2-Cl-C_6H_4$ | $COOC_2H_5$ | $CO-(2-Cl-C_6H_4)$ | 37-40 (petroleum ether) | 1715, 1685, 1675 |
| 2.22 | $C_6H_5$ | $4-Cl-C_6H_4$ | $CO-C_6H_5$ | 216-8 (ethyl ether) | 1690, 1660 |
| 2.23 | $2-Cl-C_6H_4$ | $COOC_2H_5$ | $CO-(4-CH_3O-C_6H_4)$ | 130-2 (ethyl ether) | 1740, 1710, 1680, 1665 |
| 2.24 | $C_6H_5$ | $4-Cl-C_6H_4$ | $CO-(4-Cl-C_6H_4)$ | 190-1 (ethyl ether) | 1685, 1665 |
| 2.25 | $4-Cl-C_6H_4$ | $4-Cl-C_6H_4$ | $CO-C_6H_5$ | 183-5 (ethyl ether) | 1685, 1665 |
| 2.26 | $4-CH_3O-C_6H_4$ | $COOC_2H_5$ | $CO-(4-CH_3-C_6H_4)$ | 135-8 (ethyl ether) | 1735, 1715, 1675 |
| 2.27 | $4-CH_3O-C_6H_4$ | $COOC_2H_5$ | $CO-(4-CH_3O-C_6H_4)$ | 134-5 (ethylether-petroleum ether) | 1735, 1675, 1655 |
| 2.28 | $4-Cl-C_6H_4$ | $COOC_2H_5$ | $CO-(4-CH_3-C_6H_4)$ | 126-7 (ethylacetate-petroleum ether) | 1715, 1685, 1665 |
| 2.29 | $4-Cl-C_6H_4$ | $COOC_2H_5$ | $CO-(4-CH_3O-C_6H_4)$ | 144-5 (ethylacetate-petroleum ether) | 1715, 1685, 1665 |
| 2.30 | $4-Cl-C_6H_4$ | $COOCH_3$ | $CO-C_6H_5$ | 128-30 (diisopropyl ether) | 1740, 1680, 1670 |
| 2.31 | $4-Cl-C_6H_4$ | $COOCH_3$ | $CO-(4-Cl-C_6H_4)$ | 148-9 (ethylether-petroleum ether) | 1745, 1730, 1690, 1620 |
| 2.32 | $t.C_4H_9$ | $C_6H_5$ | $CO-C_6H_5$ | 165-7 (isopropyl alcohol) | 1707, 1668, 1590 |
| 2.33 | $C_6H_5$ | $CO-C_6H_5$ | $CO-C_6H_5$ | 167-9 (isopropyl alcohol) | 1685, 1680, 1665, 1595, 1578 |
| 2.34 | $4-Cl-C_6H_4$ | $C_6H_5$ | $CO-C_4H_9(t)$ | 130-2 (isopropyl alcohol) | 1705, 1660, 1590, 1530 |
| 2.35 | $4-Cl-C_6H_4$ | $4-Cl-C_6H_4$ | $CO-C_4H_9(t)$ | 124-5 (isopropyl alcohol) | 1705, 1670, 1590, 1520 |
| 2.36 | $C_6H_5$ | $4-Cl-C_6H_4$ | $CO-C_4H_9(t)$ | oil | 1705, 1675, 1595, 1510 |
| 2.37 | $C_6H_5$ | $C_6H_5$ | $CO-C_4H_9(t)$ | 105-6 (isopropyl alcohol) | 1705, 1670, 1590, 1520 |
| 2.38 | $t.C_4H_9$ | $CH_3$ | $CO-C_6H_5$ | 82-4 (isopropyl alcohol) | 1705, 1670, 1530, 1505 |
| 2.39 | $C_6H_5$ | $CH_3$ | $CO-C_6H_5$ | 121-3 (isopropyl alcohol) | 1690, 1675, 1595, 1575 |
| 2.40 | $2,4-Cl_2-C_6H_3$ | $C_6H_5$ | $CO-C_4H_9(t)$ | 119-20 (isopropyl alcohol) | 1708, 1675, 1580, 1540 |
| 2.41 | $4-Cl-C_6H_4$ | $CH_3$ | $CO-C_6H_5$ | 158-9 (isopropyl alcohol) | 1695, 1660, 1595, 1585 |
| 2.42 | $4-Cl-C_6H_4$ | $CH_3$ | $CO-C_4H_9(t)$ | 112-3 (isopropyl alcohol) | 1712, 1660, 1590, 1490 |
| 2.43 | $C_6H_5$ | $CH_3$ | $CO-C_6H_5$ | 82-3 (isopropyl alcohol) | 1710, 1665, 1500, 1492 |
| 2.44 | $4-Cl-C_6H_4$ | $nC_3H_7-O-CH_2$ | $CO-C_6H_5$ | oil | 1680, 1675, 1595, 1587 |
| 2.45 | $2,4-Cl_2-C_6H_3$ | $nC_3H_7-O-CH_2$ | $CO-C_6H_5$ | oil | 1695, 1680, 1593, 1580 |
| 2.46 | $t.C_4H_9$ | $C_6H_5$ | $CO-C_6H_5$ | 72-5 (isopropyl alcohol) | 1720, 1710, 1625, 1590 |
| 2.47 | $4-F-C_6H_4$ | $CH_3$ | $CO-C_4H_9(t)$ | oil | 1715, 1670, 1590, |

TABLE 2-continued

Compounds of formula (I):

$$R-\underset{\underset{O}{\|}}{C}-\underset{\underset{N}{|}}{CH}-CH-R''$$
  with R' on the middle CH and a triazole-type ring (N-N, O) attached.

(I)

| Compound | R | R' | R'' | (2) m.p.(°C.) crystallization solvent | (3) IR (nujol) ($v$, cm$^{-1}$) |
|---|---|---|---|---|---|
| 2.48 | t.C$_4$H$_9$ | CH$_3$ | CO—(4-Cl—C$_6$H$_4$) | oil | 1495 1705, 1675, 1587, 1507 |
| 2.49 | 4-Cl—C$_6$H$_4$ | CH$_3$—O—CH$_2$ | CO—C$_4$H$_9$(t) | oil | 1683, 1670, 1590, 1580 |
| 2.50 | 2,4-Cl$_2$—C$_6$H$_3$ | CH$_3$ | CO—C$_4$H$_9$(t) | oil | 1715, 1675, 1600, 1493 |

EXAMPLE 6

Determination of the fungicide activity against Cucumber oidium [*Sphaeroteca fuliginea* (Schlech) Salmon]

Preventive activity:

Cucumber plants cv. Marketer, grown in pot in a conditioned environment, were sprayed on the lower leaf face with the product under examination in a water-acetone solution containing 20% of acetone (vol./vol.).

Then the plants were kept in a conditioned environment for 6 days and at the seventh day they were sprayed on the upper leaf face with an aqueous suspension of conidia of *Sphaerotheca fuliginea* (200,000 conidia/ml.). The plants were then carried back to the conditioned room.

At the end of the incubation period of the fungus, 8 days, the infection degree was evaluated and expressed by means of a scale of values from 100 (=sound plant) to 0 (=completely infected plant).

Curative activity:

Cucumber plants cv. Marketer, grown in pot in a conditioned environment, were sprayed on the upper leaf face with an aqueous suspension of conidia of *Sphaerotheca fuliginea* (200,000 conidia/ml. After 24 hours from the infection the plants were treated with the product under examination in a water-acetone solution containing 20% of acetone (vol./vol.), by spraying both leaf faces. At the end of the incubation period of the fungus (8 days), during which time the plants were kept in a suitably conditioned environment, the infection degree was evaluated and expressed by means of a scale of values from 100 (=sound plant) to 0 (=completely infected plant).

The data relating to the fungicide activity against Cucumber oidium of some compounds of formula I, in comparison with a compound according to British Pat. No. 1,511,956, are recorded in the following Table 3.

TABLE 3

Fungicide activity against Cucumber oidium at the indicated doses, expressed according to a scale from 100 (= sound plant) to 0 (= completely infected plant).

| Compound (see Table 2) | Dose a.i. (g/l) | Preventive activity | Curative activity |
|---|---|---|---|
| 2.2 | 0.5 | 100 | 100 |
|  | 0.25 | 100 | 100 |
|  | 0.125 | 100 | 100 |
|  | 0.06 | 70 | 90 |
| 2.6 | 0.5 | 100 | 100 |
|  | 0.25 | 100 | 100 |
|  | 0.125 | 100 | 100 |
|  | 0.06 | 100 | 100 |
|  | 0.03 | 100 | 100 |
| 2.7 | 0.5 | 100 | 100 |
|  | 0.25 | 100 | 100 |
|  | 0.125 | 100 | 100 |
|  | 0.06 | 80 | 90 |
| 2.9 | 0.5 | 100 | 100 |
|  | 0.25 | 100 | 100 |
|  | 0.125 | 100 | 100 |
|  | 0.06 | 100 | 100 |
| 2.12 | 0.5 | 100 | 100 |
|  | 0.25 | 100 | 100 |
|  | 0.125 | 100 | 100 |
|  | 0.06 | 100 | 100 |
| 2.13 | 0.5 | 100 | 100 |
|  | 0.25 | 100 | 100 |
|  | 0.125 | 100 | 100 |
|  | 0.06 | 100 | 100 |
| 2.14 | 0.5 | 100 | 100 |
|  | 0.25 | 100 | 100 |
|  | 0.125 | 100 | 100 |
|  | 0.06 | 100 | 100 |
| 2.15 | 0.5 | 100 | 100 |
|  | 0.25 | 100 | 100 |
|  | 0.125 | 100 | 100 |
|  | 0.06 | 100 | 100 |
| 2.16 | 0.5 | 100 | 100 |
|  | 0.25 | 100 | 100 |
|  | 0.125 | 100 | 100 |
|  | 0.06 | 100 | — |
| 2.19 | 0.5 | 100 | 100 |
|  | 0.25 | 100 | 100 |
|  | 0.125 | 100 | 100 |
| 2.21 | 0.5 | 100 | 100 |
|  | 0.25 | 100 | 100 |
|  | 0.125 | 100 | 100 |
| 2.23 | 0.5 | 100 | 100 |
|  | 0.25 | 100 | 100 |
|  | 0.125 | 100 | 100 |
|  | 0.06 | 100 | — |
| 2.26 | 0.5 | 100 | 100 |
|  | 0.25 | 100 | 100 |
|  | 0.125 | 100 | 100 |
| 2.27 | 0.5 | 100 | 100 |
|  | 0.25 | 100 | 100 |
|  | 0.125 | 100 | 100 |
| 2.28 | 0.5 | 100 | 100 |
|  | 0.25 | 100 | 100 |
|  | 0.125 | 100 | 100 |

TABLE 3-continued

Fungicide activity against Cucumber oidium at the indicated doses, expressed according to a scale from 100 (= sound plant) to 0 (= completely infected plant).

| Compound (see Table 2) | Dose a.i. (g/l) | Preventive activity | Curative activity |
|---|---|---|---|
| | 0.06 | 100 | 100 |
| 2.29 | 0.5 | 100 | 100 |
| | 0.25 | 100 | 100 |
| | 0.125 | 100 | 100 |
| | 0.06 | 100 | 100 |
| 2.30 | 0.5 | 100 | 100 |
| | 0.25 | 100 | 100 |
| 2.31 | 0.5 | 100 | 100 |
| | 0.25 | 100 | 100 |
| | 0.125 | 100 | 100 |
| 2.34 | 0.5 | 100 | 100 |
| | 0.25 | 100 | 100 |
| | 0.125 | 100 | 100 |
| | 0.06 | 100 | 100 |
| 2.35 | 0.5 | 100 | 100 |
| | 0.25 | 100 | 100 |
| | 0.125 | 100 | 100 |
| | 0.06 | 100 | 100 |
| 2.36 | 0.5 | 100 | 100 |
| | 0.25 | 100 | 100 |
| | 0.125 | 100 | 100 |
| | 0.06 | 100 | 100 |
| 2.37 | 0.5 | 100 | 100 |
| | 0.25 | 100 | 100 |
| | 0.125 | 100 | 100 |
| | 0.06 | 100 | 100 |
| 2.39 | 0.5 | 100 | 100 |
| | 0.25 | 100 | 100 |
| | 0.125 | 100 | 100 |
| | 0.06 | 100 | 100 |
| 2.40 | 0.5 | 100 | 100 |
| | 0.25 | 100 | 100 |
| | 0.125 | 100 | 100 |
| | 0.06 | 100 | 100 |
| 2.41 | 0.5 | 100 | 100 |
| | 0.25 | 100 | 100 |
| | 0.125 | 100 | 100 |
| | 0.06 | 100 | 100 |
| 2.42 | 0.5 | 100 | 100 |
| | 0.25 | 100 | 100 |
| | 0.125 | 100 | 100 |
| | 0.06 | 100 | 100 |
| 2.43 | 0.5 | 100 | 100 |
| | 0.25 | 100 | 100 |
| | 0.125 | 100 | 100 |
| | 0.06 | 85 | 100 |
| 2.46 | 0.5 | 100 | 100 |
| | 0.25 | 100 | 100 |
| | 0.125 | 100 | 100 |
| | 0.06 | 100 | 100 |
| Comparison(*) | 0.5 | 90 | 100 |
| | 0.25 | 50 | 85 |
| | 0.125 | 10 | 76 |
| | 0.06 | 0 | 0 |

(*)The compound 2-(1,2,4-triazol-1-yl)-1,4-(di-4-chlorophenyl)-butan-1,4-dione of formula:

described in example 1 of British Patent Application No 1,511,956, was used as comparison compound.

EXAMPLE 7

Determination of the systemic fungicide activity against Cucumber oidium [*Sphaeroteca fuliginea* (Schlech) Salmon]

Cucumber plants cv. Marketer grown in pot in a conditioned environment were treated by adding to the soil in the pot a water dispersion of the tested product in the selected concentration. 24 hours after the treatment, the plants were sprayed on the upper leaf face with an aqueous suspension of conidia of *Sphaeroteca fuliginea* (200.000 conidia/ml). The infected plants were kept in a conditioned environment for the incubation of the fungus (8 days). At the end of such period of time, the infection degree was evaluated and expressed by means of a scale of values from 100 (=sound plant) to 0 (=completely infected plant), using as a control infected but not treated plants. Compounds 2.42 and 2.43 (see Table 2) showed a complete systemic fungicidal activity (rated 100) at the dose of 0.5 g/l.

EXAMPLE 8

Determination of the fungicide activity against bean-rust [*Uromyces appendiculatus* (Pers.) Link]

Preventive activity:

Bean plants cv. Borlotto di Vigevano grown in pot in a conditioned environment were sprayed on both leaf faces with the product being tested in a water-acetone solution (acetone 20% by volume).

The treated plants were kept for 24 hours in a conditioned environment (23° C. and 70% relative humidity). Thereafter, the plants were sprayed on the lower leaf face with a suspension of spores of *Uromyces appendiculatus* (200.000 spores/ml). The infected plants were kept 24 hours in a humidity saturated environment, then were transferred back into the conditioned environment.

After 14 days, that is after the incubation of the fungus, the infection degree was evaluated and expressed by means of a scale of values from 100 (=sound plant) to 0 (=completely infected plant), using as a control infected but not treated plants. Compounds 2.42 and 2.43 (see Table 2) showed a complete fungicidal activity (rated 100) at the dose of 0.5 g/l.

What we claim is:

1. A compound of formula $$R-\underset{\underset{O}{\|}}{C}-\underset{\underset{N-N}{|}}{CH}-\underset{}{CH}-R^2 \quad \text{with triazole ring}$$

in which:

R is selected from the group consisting of phenyl, phenyl substituted by at least one group selected from $C_1$-$C_4$ alkyl, $C_1$-$C_4$ alkoxy, and halogen atoms;

R' is selected from the group consisting of phenyl, $C_1$-$C_4$ alkyl, —COOR substituted by $C_1$-$C_4$ alkyl; and $R^2$ is a phenyl carbonyl group, a phenyl carbonyl group in which the phenyl is substituted by at least one substituent selected from the group consisting of $C_1$-$C_4$ alkyl, $C_1$-$C_4$ alkoxy and halogen atoms.

2. A fungicidal composition comprising as active ingredient an effective amount of at least one compound as defined in claim 1, and an inert solid or liquid carrier.

3. A method of controlling fungus infections in useful plants, consisting in distributing on the plants or in the area where they grow, when the fungus infection is foreseen or is already in progress, an effective amount of a fungicidal compound as defined in claim 1, as such or in the form of a composition suitable for agrarian use.

4. A method of controlling fungus infections in useful plants, according to claim 3, applied to the control of fungus infections known as oidium.

* * * * *